US010068334B2

(12) United States Patent
Wang et al.

(10) Patent No.: US 10,068,334 B2
(45) Date of Patent: Sep. 4, 2018

(54) RECONSTRUCTION OF IMAGES FROM AN IN VIVO MULTI-CAMERA CAPSULE

(71) Applicants: CAPSO VISION, INC., Saratoga, CA (US); Kang-Huai Wang, Saratoga, CA (US); Chenyu Wu, Sunnyvale, CA (US)

(72) Inventors: Kang-Huai Wang, Saratoga, CA (US); Chenyu Wu, Sunnyvale, CA (US)

(73) Assignee: CAPSOVISION INC, Saratoga, CA (US)

( * ) Notice: Subject to any disclaimer, the term of this patent is extended or adjusted under 35 U.S.C. 154(b) by 374 days.

(21) Appl. No.: 14/775,711

(22) PCT Filed: May 19, 2014

(86) PCT No.: PCT/US2014/038533
§ 371 (c)(1),
(2) Date: Sep. 13, 2015

(87) PCT Pub. No.: WO2014/193670
PCT Pub. Date: Dec. 4, 2014

(65) Prior Publication Data
US 2016/0037082 A1 Feb. 4, 2016

Related U.S. Application Data

(60) Provisional application No. 61/828,653, filed on May 29, 2013.

(51) Int. Cl.
H04N 9/47 (2006.01)
H04N 7/18 (2006.01)
(Continued)

(52) U.S. Cl.
CPC ........ *G06T 7/0014* (2013.01); *A61B 1/00009* (2013.01); *A61B 1/041* (2013.01); *G06T 5/006* (2013.01); *G06T 7/11* (2017.01); *G06T 7/13* (2017.01); *G06T 7/136* (2017.01); *G06T 7/174* (2017.01); *G06T 7/337* (2017.01); *G06T 7/37* (2017.01); *G06T 7/40* (2013.01);
(Continued)

(58) Field of Classification Search
None
See application file for complete search history.

(56) References Cited

U.S. PATENT DOCUMENTS

2002/0154812 A1 10/2002 Chen
2005/0215876 A1* 9/2005 Chen ................. A61B 1/041
600/407
(Continued)

Primary Examiner — Talha M Nawaz
(74) Attorney, Agent, or Firm — Blairtech Solution LLC

(57) ABSTRACT

Method and apparatus of reconstruction of images from an in vivo multi-camera capsule are disclosed. In one embodiment of the present invention, the capsule comprises two cameras with overlapped fields of view (FOVs). Intra-image based pose estimation is applied to the sub-images associated with the overlapped area to improve the pose estimation for the capsule device. In another embodiment, two images corresponding to the two FOVs are fused by using disparity-adjusted, linear weighted sum of the overlapped sub-images. In yet another embodiment, the images from the multi-camera capsule are stitched for time-space representation.

33 Claims, 15 Drawing Sheets

(51) Int. Cl.
  *G06T 7/00* (2017.01)
  *A61B 1/00* (2006.01)
  *A61B 1/04* (2006.01)
  *G06T 11/60* (2006.01)
  *H04N 5/225* (2006.01)
  *H04N 5/232* (2006.01)
  *H04N 5/247* (2006.01)
  *H04N 5/265* (2006.01)
  *G06T 5/00* (2006.01)
  *G06T 7/73* (2017.01)
  *G06T 7/13* (2017.01)
  *G06T 7/40* (2017.01)
  *G06T 7/33* (2017.01)
  *G06T 7/37* (2017.01)
  *G06T 7/11* (2017.01)
  *G06T 7/174* (2017.01)
  *G06T 7/136* (2017.01)

(52) U.S. Cl.
  CPC ............... *G06T 7/73* (2017.01); *G06T 11/60* (2013.01); *H04N 5/2252* (2013.01); *H04N 5/23229* (2013.01); *H04N 5/247* (2013.01); *H04N 5/265* (2013.01); *G06T 2207/10068* (2013.01); *G06T 2207/20048* (2013.01); *G06T 2207/20072* (2013.01); *G06T 2207/20081* (2013.01); *G06T 2207/20221* (2013.01); *G06T 2207/30004* (2013.01); *G06T 2207/30028* (2013.01); *G06T 2207/30032* (2013.01)

(56) References Cited

U.S. PATENT DOCUMENTS

| | | | |
|---|---|---|---|
| 2007/0116119 A1* | 5/2007 | Wang | H04N 19/503 375/240.12 |
| 2008/0208006 A1 | 8/2008 | Farr | |
| 2009/0010507 A1 | 1/2009 | Geng | |
| 2009/0074265 A1 | 3/2009 | Huang et al. | |
| 2009/0278921 A1* | 11/2009 | Wilson | A61B 1/00177 348/77 |
| 2009/0284589 A1* | 11/2009 | Radeva | G06T 7/0012 348/77 |
| 2010/0010300 A1* | 1/2010 | Gilad | A61B 1/00158 600/109 |
| 2011/0085022 A1* | 4/2011 | Wang | A61B 1/0005 348/36 |

* cited by examiner

RECONSTRUCTION OF IMAGES FROM AN IN VIVO MULTI-CAMERA CAPSULE

CROSS REFERENCE TO RELATED APPLICATIONS

The present invention claims priority to U.S. Provisional Patent Application, Ser. No. 61/828,653, entitled "Reconstruction of Images from an in vivo Multi-Cameras Capsule", filed on May 29, 2013. The present invention is related to U.S. patent application Ser. No. 11/642,275, entitled "In Vivo Image Capturing System Including Capsule Enclosing A Camera", filed on Dec. 19, 2006, U.S. patent application Ser. No. 12/323,219 entitled "Camera System with Multiple Pixel Arrays on a Chip", filed on Nov. 25, 2008, U.S. Pat. No. 7,817,354, entitled "Panoramic Imaging System", issued on Oct. 19, 2010 and U.S. patent application Ser. No. 13/626,168 entitled "Camera System with Multiple Pixel Arrays on a Chip", filed on Sep. 25, 2012. The U.S. Provisional Patent Application, U.S. patent applications and US patent are hereby incorporated by reference in their entireties.

FIELD OF THE INVENTION

The present invention relates to image reconstruction from images captured using in vivo capsule with multiple cameras.

BACKGROUND

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, and are invasive and uncomfortable for the patient. Their cost restricts their application as routine health-screening tools.

Because of the difficulty traversing a convoluted passage, endoscopes cannot reach the majority of the small intestine. Therefore, special techniques and precautions are required to reach the entirety of the colon, which will add cost. Endoscopic risks include the possible perforation of the bodily organs traversed and complications arising from anesthesia. Moreover, a trade-off must be made among patient pain during the procedure, the health risks and post-procedural down time associated with anesthesia. Endoscopies are necessarily inpatient services that involve a significant amount of time from clinicians and thus are costly.

An alternative in vivo image sensor that addresses many of these problems is capsule endoscope. A camera is housed in a swallowable capsule along with a radio transmitter for transmitting data to a base-station receiver or transceiver. A data recorder outside the body may also be used to receive and record the transmitted data. The data primarily comprises images recorded by the digital camera. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. patent application Ser. No. 11/533,304, entitled "In Vivo Autonomous Camera with On-Board Data Storage or Digital Wireless Transmission in Regulatory Approved Band," filed on Sep. 19, 2006. This application describes a capsule system using on-board storage such as semiconductor nonvolatile archival memory to store captured images. After the capsule passes from the body, it is retrieved. Capsule housing is opened and the images stored are transferred to a computer workstation for storage and analysis. For capsule images either received through wireless transmission or retrieved from on-board storage, the images will have to be displayed and examined by diagnostician to identify potential anomalies.

Besides the above mentioned forward-looking capsule cameras, there are other types of capsule cameras that provide side view or panoramic view. A side or reverse angle is required in order to view the tissue surface properly. Conventional devices are not able to see such surfaces, since their field of view (FOV) is substantially forward looking. It is important for a physician to see all areas of these organs, as polyps or other irregularities need to be thoroughly observed for an accurate diagnosis. Since conventional capsules are unable to see the hidden areas around the ridges, irregularities may be missed, and critical diagnoses of serious medical conditions may be flawed. A camera configured to capture a panoramic image of an environment surrounding the camera is disclosed in U.S. patent application Ser. No. 11/642,275, entitled "In vivo sensor with panoramic camera" and filed on Dec. 19, 2006. The panoramic camera system is configured with a longitudinal field of view (FOV) defined by a range of view angles relative to a longitudinal axis of the capsule and a latitudinal field of view defined by a panoramic range of azimuth angles about the longitudinal axis such that the camera can capture a panoramic image covering substantially a 360° latitudinal FOV.

Conceptually, multiple individual cameras may be configured to cover completely or substantially a 360° latitudinal FOV. However, such panoramic capsule system may be expensive since multiple image sensors and associated electronics may be required. A cost-effective panoramic capsule system is disclosed in U.S. patent application Ser. No. 11/624,209, entitled "Panoramic Imaging System", filed on Jan. 17, 2007. The panoramic capsule system uses an optical system configured to combine several fields-of-view to cover a 360° view. Furthermore, the combined fields-of-view is projected onto a single sensor to save cost. Therefore, this single sensor capsule system functions effectively as multiple cameras at a lower cost. The sensor structure and operation to support panoramic view is further described in U.S. patent application Ser. No. 12/323,219 entitled "Camera System with Multiple Pixel Arrays on a Chip", filed on Nov. 25, 2008 and U.S. patent application Ser. No. 13/626, 168, entitled "Camera System with Multiple Pixel Arrays on a Chip", filed on Sep. 25, 2012.

In an autonomous capsule system, multiple images along with other data are collected during the course when the capsule camera travels through the gastrointestinal (GI) tract. The images and data are usually displayed on a display device for a diagnostician or medical professional to examine. In order to increase the efficiency of examination, the images are displayed continuously as a video with some display control such as display speed, Forward, Reverse, and Stop to allow a user to navigate through the image sequence easily. Presenting the set of collected images as video data can substantially improve the efficiency of examination. However, each image only provides a limited view of a small section of the GI tract. It is desirable to combine the capsule images as a large picture representing a cut-open view of the inner GI tract surface. The large picture can take advantage of the high-resolution large-screen display device to allow a user to visualize more information at the same time. After removing the redundant overlapped areas between images, a larger area of the inner GI tract surface can be viewed at the same time. In addition, the large picture can provide a complete view or a significant portion of the inner GI tract surface. It should be easier and faster for a diagnostician or a medical professional to quickly spot an area of interest, such as a polyp.

DETAILED DESCRIPTION OF THE INVENTION

Figure 1A:
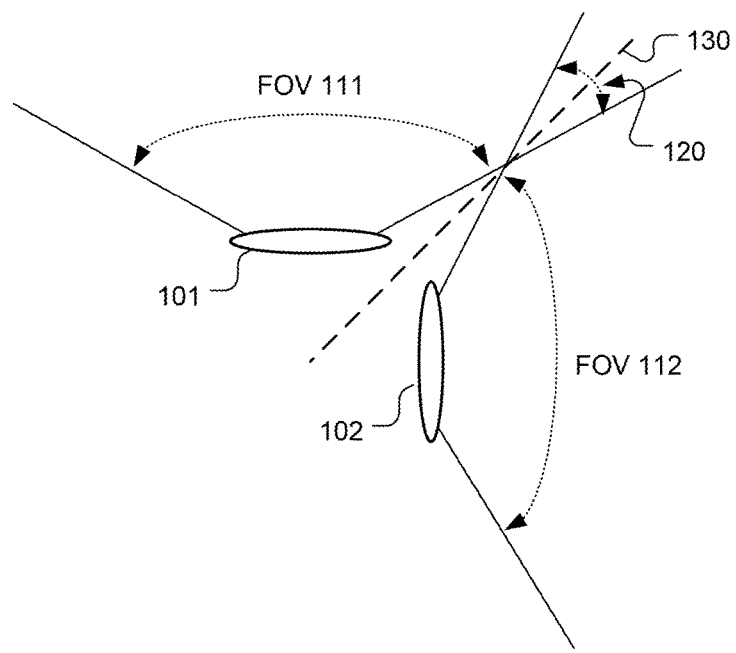
FIG. 1A illustrates an exemplary configuration of two cameras with overlapped fields of view.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely a representative of selected embodiments of the invention. References throughout this specification to "one embodiment," "an embodiment," or similar language mean that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention. The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

During the course of imaging through the human GI tract, an autonomous capsule camera often captures tens of thousands of images. Each image corresponds to the scene within the field of view of the camera optics. The capsule may have a forward looking camera or a side view camera. In either case, each image corresponds to a very small area or section of the surface of the GI tract. In the field of computational photography, image mosaicing techniques have been developed to stitch smaller images into a large picture. The technique has been used in consumer digital camera to allow a user to capture panoramic picture by panning the camera around. A fully automatic construction of panoramas is disclosed by Brown and Lowe in a paper entitled "Recognising Panoramas", *Proceedings of Ninth IEEE International Conference on Computer Vision*, Vol. 2, Pages 1218-1225, 13-16 Oct. 2003. Brown and Lowe use image matching techniques based on rotation and scale invariant local features to select matching images, and a probabilistic model for verification. The method is insensitive to the ordering, orientation, scale and illumination of the images and also insensitive to noisy images. A review of general technical approaches to image alignment and stitching can be found in "Image Alignment and Stitching: A Tutorial", by Szeliski, Microsoft Research Technical Report MSR-TR-2004-92, Dec. 10, 2006.

For image mosaicing, corresponding parts, objects or areas among images are identified first. After corresponding parts, objects or areas are identified, the images can be stitched by aligning the corresponding parts, objects or areas. Two images can be matched directly in the pixel domain and the pixel-based image matching is also called direct match. However, it will involve very intensive computations. An alternative approach is to use feature-based image matching. A set of feature points are determined for each image and the matching is performed by comparing the corresponding feature descriptors. The number of feature points is usually much smaller than the number of pixels of a corresponding image. Therefore, the computational load for feature-based image matching is substantially less that for pixel-based image matching. However, it is still time consuming for pair-wise matching. Usually k-d tree is utilized to speed up this procedure. Accordingly, feature-based image matching is widely used in the field. Nevertheless, the feature-based matching may not work well for some images. In this case, the direct image matching can always be used as a fall back mode, or a combination of the above two approaches can be preferred.

Upon determining the feature points in two images, the two feature sets are matched by identifying the best matching between the two sets under a selected criterion. The feature points correspond to some distinct features in the scene that is not be planar. The matching may have to take into account of three-dimensional geometrical aspect of objects in the scene during image capture of the two images. Therefore, the two sets of feature points are matched according to a mathematical model beyond two-dimensional translation. There are various transformation models to relate the two sets of feature points. One often used rigid model involves rotation as well as translation. Let $x_i$ (i∈[1,m]) and $y_j$(j∈[1,q]) be 3×1 column vectors corresponding to feature points of images IA and IB respectively. X and Y are 3×m and 3×q matrices with $x_i$ and $y_j$ as respective column vectors. The feature point $y_j$ is matched with a corresponding $x_i$ according to $Ry_{j(P)} - t \leftrightarrow x_i$, where R represents the 3×3 rotation matrix, t represents the 3×1 translation vector, and P corresponds to an m×q permutation matrix, where pij=1 if $x_i$ matches $y_j$, and 0 otherwise. If $L_2$ (squared) error measure is used, the $L_2$ error for a given rotation R, translation t and permutation P is:

$$d(X, Y | P, R, t) = \frac{1}{m} \sum_{i=1}^{m} \|x_i - Ry_{j(p)} - t\|^2. \tag{1}$$

If a 3×q matrix T is defined as T=[t, t, . . . , t], the above equation can be rewritten as:

$$d(X, Y | P, R, T) = \frac{1}{m} \|X - (RY - T)P^T\|^2. \tag{2}$$

A best match between the two feature sets can be found by minimizing the error metric in equation (2) over all possible rotations and permutations simultaneously, which may cause a formidable computational load. To overcome the computational complexity issue associated with simultaneous optimization over rotation and permutation, the optimization procedure can be broken down into two sub-problems and solved using iterative procedure as described in "The 3D-3D Registration Problem Revisited", by Li et al., *Proceedings of IEEE 11th International Conference on Computer Vision*, Pages 1-8, Oct. 14-21, 2007. Given image information, the permutation step to find correspondences can be simplified by applying image matching. Finding best transformation is usually implemented by RANdom Sample Consensus (RANSAC) and least median of squares (LMS).

Beside the rotation model for feature-based image registration, there are other transformation models to describe feature point relation among multiple images. For example, in "Image Alignment and Stitching: A Tutorial", by Szeliski, Microsoft Research Technical Report MSR-TR-2004-92, Dec. 10, 2006, described a model involves rotation and camera focal length associated with each image. A rotation matrix and focal length update procedure is then used to identify a best match. For the stitching problem, only 2D image coordinates are considered. The transformation between two sets of image points can be computed using the following equation:

$$u_i = H_{ij}u_j, H_{ij} = K_i R_i R_j^T K_j^{-1}, \tag{3}$$

$u_i$ and $u_j$ are homogeneous coordinates for $u_i=[x_i,y_i,1]$, $u_j=[x_j,y_j,1]$. K is the 3×3 camera intrinsic matrix which includes focal length and other camera parameters. $R_i$ and $R_j$ are 3×3 rotation matrices for each camera. $H_{ij}$ is the 3×3 transformation matrix between two images and it is also known as homography. More generally, $H_{ij}$ can have two unknowns (translation), four unknowns (translation+rotation), 6 unknowns (affine), or 8 unknowns (projective). In general, homography represents a linear transformation between two images.

For capsule camera applications, a series of images are collected during the course of traveling through the GI tract. It is desirable to be able to recognize and match corresponding parts, objects or areas, and stitch the images to form a larger composite picture for viewing. The techniques for recognizing, matching and stitching images mentioned above are relevant to the capsule camera application. However, for capsule images, the situation is more challenging. First, the object distance (GI tract surface to the camera) is usually very close. The commonly used affine camera model is an approximation which is only valid when the set of points seen in the image has small depth variation compared with the distance from the camera. In the capsule camera system environment, the short distance between the lumen wall and the camera as well as uneven lumen wall due to folds or other reasons cause the affine camera model invalid. A more complicated model such as projective model should be considered instead.

Besides the distance issue, the peristalsis of the GI tract will cause apparent motion in the captured images. Such a local deformation cannot be dealt with linear transformation described earlier. A non-linear transformation function $f$ will replace the transformation matrix $H_{ij}$ in equation (3), i.e., $u_i = f(u_j)$. Such non-linear transformation functions include thin-plate, radial basis functions, etc. Solving this problem involves a very complicated non-linear optimization procedure. On the other hand, since the frame rate of capsule images is relatively low (in the order of one frame every few seconds to a few frames every second), the motion between consecutive images may be noticeable. In most image matching studies, the scene is assumed to be static with some moving objects. The areas covered by moving objects usually are small with respect to the overlapped region. Therefore, there will be always some overlapped static areas to allow reasonable performance for image matching. On the other hand, two consecutive capsule images may correspond to two distinct scenes of lumen wall sometimes due to deformation of the lumen wall and camera movement. One method according to the present invention improves the reliability of the camera model by using multiple cameras within the capsule to simultaneously capture multiple capsule images, where the multiple images are overlapped. Since the overlapped areas of two images are captured at the same time instance, there is no relative motion involved between the two overlapped areas. Therefore, for each time instance, a more reliable rigid camera model can be derived for the overlapped areas without the concern of any motion between the overlapped areas for multiple cameras. Once a bigger picture is composed for each time instance, more overlapped areas can be used for stitching between different time frames. It has been observed that images corresponding to some sections of the GI tract contain few features. In one embodiment of the prevent invention, derivation of image features may be based on image intensity, gradient and shading information. Calibration of near-field lighting is also required.

Figure 1B:
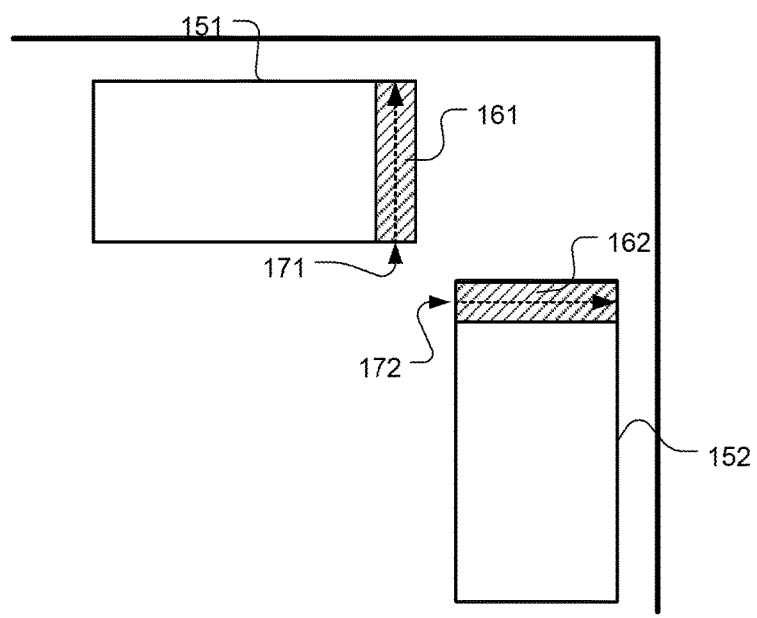
FIG. 1B illustrates an exemplary configuration of image sensor arrays to capture images from the two cameras in FIG. 1A.

FIG. 1A illustrates an exemplary multiple-camera arrangement according to an embodiment of the present invention. Lens 101 and lens 102 project respective scenes in the fields of view (FOVs) 111 and 112 onto respective parts of the image sensor. FOV 111 and FOV 112 have an overlapped area 120. The scenes corresponding to lenses 101 and 102 are projected onto respective parts of the image sensor 151 and 152 as shown in FIG. 1B. The scene in the overlapped area 120 will be projected to area 161 of the image sensor 151 as well as area 162 of the image sensor 152 as shown in FIG. 1B. The dashed arrows 171 and 172 represent the middle line of the overlapped area 120. Both lens 101 and 102 are disposed fixedly within the capsule housing, which is not shown in FIG. 1A. Therefore, the relative location and orientation of the two lenses are maintained. The optical system of the cameras in the capsule can be calibrated to properly align the two lenses. After calibration, the center line 130 for the overlapped area will be projected to known locations 171 and 172 of the image sensors. According to one arrangement of the present invention, image sensor sub-areas 151 and 152 can be properly positioned so that locations 171 and 172 correspond to the middle of the overlapped area. In the case of surrounding surfaces having various distances to cameras, the dashed arrows 171 and 172 may not be located in the middle line of the overlapped area 161 and 162. The multiple camera arrangement shown in FIG. 1A can provide an extended field of view by combining the two images corresponding to two respective fields of view.

Overlapped area in each image can be derived or constrained by the camera pose position. Moreover, the camera pose parameters can be used to initialize the transformation between images. In yet another embodiment of the present invention, one side of capsule is contacting the GI tract wall. Therefore, the imaging surface is a part of a cylinder. The overlapped area can be determined by the overlapped field of view of two adjacent cameras. In one embodiment, the image matching can be optimized down to sub-pixel. In another embodiment, the camera pose position of the multiple cameras can be derived using calibration images stored in the camera. In yet another embodiment such camera pose parameters can be used to constrain the transformation between images.

Intra Image Stitching

Figure 2:
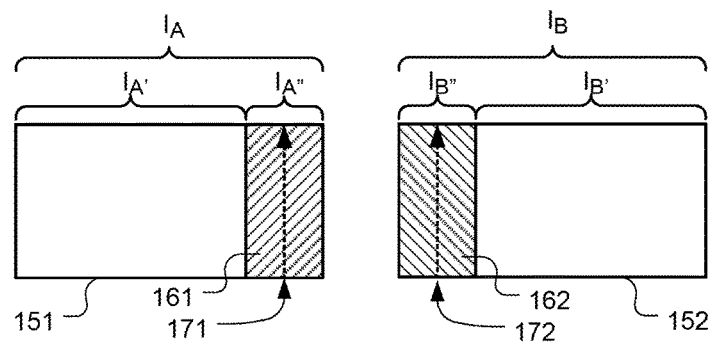
FIG. 2 illustrates the non-overlapped and overlapped areas of the captured images for the two cameras of FIG. 1A.

FIG. 2 illustrates some naming conventions used in this disclosure. Images $I_A$ and $I_B$ represent the two images captured by the image sensor sub-area 151 and 152 respectively. Each image consists of a non-overlapped area ($I_{A'}$ or $I_{B'}$) and an overlapped area ($I_{A''}$ or $I_{B''}$). The overlapped areas $I_{A''}$ and $I_{B''}$ can be determined to a certain accuracy after calibration. For a conventional camera system, only one image (e.g., $I_A$) is captured at a time. Image matching, registration and mosaicing are based on the corresponding image sequence $I_{Aj}$, where j is the time index of the image sequence. An exemplary system incorporating an embodiment of the present invention captures two simultaneous sequences $I_{Aj}$ and $I_{Bj}$, which include two sub-sequences $I_{Aj''}$ and $I_{Bj''}$ corresponding to the overlapped area.

Since the sub-sequences $I_{Aj''}$ and $I_{Bj''}$ correspond to the same scene, this may impose additional constraints on the matching and registration process. For example, a camera model based on rotation $R_{ABj}$ and focal length $f_{Aj}$ and $f_{Bj}$ may be used for image matching and registration between two images $I_{Aj''}$ and $I_{Bj''}$ at time instance j. In other words, we can use Eq. (3) to describe the transformation between these two images.

In a conventional system, only one sequence is captured. Feature extraction, image matching and registration are performed based on this single sequence. In a system incorporating multiple cameras according to an embodiment of the present invention, the conventional feature extraction, image matching and registration can be performed on individual image sequences. In addition, the known overlapped areas in the multiple sequences can be used to improve system performance in terms of improved reliability and/or faster algorithm convergence. Given M cameras and N images captured by each camera, there are a total of N×M images. One option is to stitch the entire set of images without any constraints. Each transformation between two images can use a non-linear model because of the local deformation of the GI tract. Another option to speed up and improve the performance is to apply two-step stitching. For each time index, there are M images from different cameras. Since they are captured at the same time, the same contents should be observed in the overlapped areas of the M images. In other words, there is no local deformation between these M images. For convenience, these M images captured by the M cameras at the same time are referred to as intra images. Therefore, M images can be stitched using a linear camera model which is much simpler and faster to solve. N composed images can be stitched using non-linear camera models. To avoid erroneous transformation, the derived H matrix for the M intra images within a composed image must be consistent with the known camera relative position of the multiple cameras. If refinement is needed, the image data stored in the camera or otherwise made available can be used for determining accurate absolute and relative position of the multiple cameras.

Images Fusing for Overlapped Area

Figure 3:
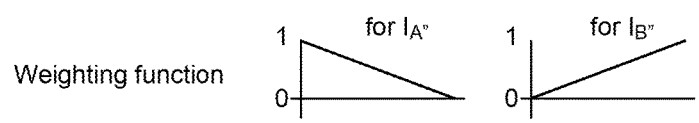
FIG. 3 illustrates an exemplary image fusing to combine two overlapped images into one wide image.
Figure 3:
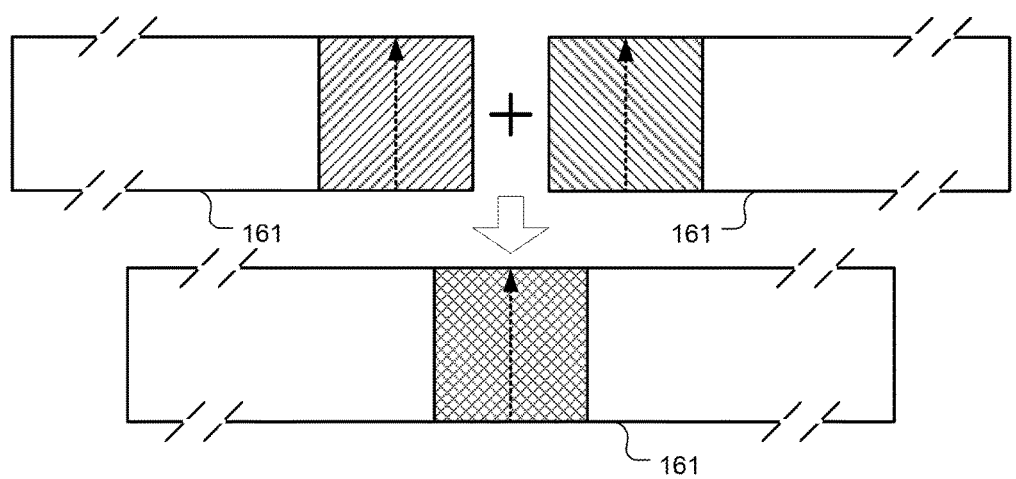

It is easier for a user to view the two images corresponding to two fields of view by "composing" a wide image using $I_{Aj}$ and $I_{Bj}$ instead of two separate images. FIG. 3 illustrates an example of image fusing using linear weighting and linear disparity adjustment according to an embodiment of the present invention. Since the camera optics are properly calibrated, so that a particular view angle for the two cameras scene in the overlapped area are aligned at the two dashed lines 171 and 172. A simple approach of image composing can be achieved by cropping and splicing at the dashed lines 171 and 172. However this may not be true for surrounding surface with various depths. Nevertheless, seamless image composing can be achieved by "fusing" the two overlapped areas. There are more advanced fusing/blending techniques, such as Laplacian pyramid blending and gradient domain blending. Basically, blending happens in different frequency domains. More details can be found in "Image Alignment and Stitching: A Tutorial", by Szeliski, Microsoft Research Technical Report MSR-TR-2004-92, Dec. 10, 2006.

Image Stitching for Sequences from Multiple Cameras

During the course of travelling through the GI tract, a capsule camera system may snap tens of thousands of pictures. For capsule systems, with either digital wireless transmission or on-board storage, the captured images will be played back for analysis and examination by a medical professional. In order to make the viewing more efficient, the captured images usually are played back continuously as a video sequence. During playback, a diagnostician may look for polyps or other points of interest as quickly and efficiently as possible. The playback may be at a controllable frame rate and may be increased to reduce viewing time. Due to the large number of images captured, it will take quite a while to look through all the images even if they are played back continuously as a video. For example, to view 30,000 images as a video sequence at 30 frames per second will require 16.67 minutes non-stop viewing. After taking into account of additional time for Pause, lower-frame playback and reverse search for close examination of possible anomaly, it will likely take 30 minutes or longer to finish the examination. A typical capsule image usually has much lower resolution than what the display device can support. Therefore, only a small portion of the display screen is usually used. Furthermore, consecutive images usually contain substantial overlapped areas. Therefore, as an alternative to displaying the images as a video sequence, the images can be stitched to form one or multiple large composite images. The large composite images correspond to a cut-open view of the internal surface of the GI tract. In another embodiment, stitched images are formed for tunnel view. The large composite image can be displayed on a high-resolution display device to allow a medical professional to quickly spot any anomaly for the entire GI tract or a good portion of the GI tract. If the composite image size is larger than the resolution of the display device, a scaled-down composite image can be displayed. Alternatively, a portion of the composite image can be displayed and a user interface is provided to allow a use to pan through the composite image.

Image stitching or image mosaicking techniques are known in the field of digital photography. A set of images are provided as input to the image stitching or image mosaicking process, where the set of images covers a scene and there are always overlapped areas between images to allow proper image alignment. Before images can be stitched, the images have to be aligned or matched. Both direct (pixel-based) alignment and feature-based registration can be used. Often, feature-based matching is used to reduce the required amount of computations. At this stage, image matching is usually performed for individual pairs in order to keep the computational load low. However, this individual matching may cause large amount of overall alignment errors. To reduce the overall alignment error, a process called Bundle Adjustment is applied to simultaneously adjust pose parameters for all images. During bundle adjustment, images that cannot be properly registered will be removed to alleviate potential artifact during image composition. After bundle adjustment, the pairwise images are ready for stitching or compositing to create a larger picture. With all images registered, the final image composition can be performed for a selected compositing surface and view. The source pixels are then mapped to the final composite surface using proper weighting and blending.

Figure 4A:
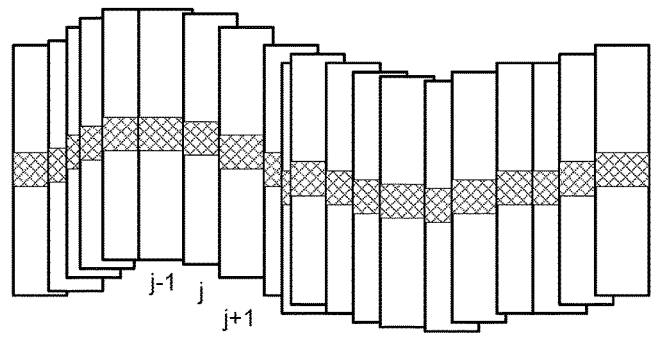
FIG. 4A illustrates the effect of capsule spin and translation for a side-view capsule camera system.

Image stitching for capsule images is more challenging than the case for digital photography due to relatively short focal length and the local movement of the GI tract walls. Furthermore, the capsule camera may spin in additional to longitudinal movement while travelling through the GI tract. FIG. 4A illustrates an example of captured images by a two-camera side-view capsule device undergoing capsule spin, where the horizontal direction corresponds to the longitudinal direction along the GI tract. The capsule spin will cause the captured images to shift perpendicular to the longitudinal direction, i.e., to shift up and down. Since the capsule device is propelled by the peristalsis of the GI tract, the amount of movement from frame to frame may not be uniform.

In a conventional approach to image stitching, the overlapped area for each pair of images is intrinsically determined during image matching. Basically feature extraction and matching will be applied across the entire image. As a result, most of matched feature pairs are located in the overlapped area. In a system according to the present invention, the overlapped area in each pair of images may be determined based on motion information. Motion estimation techniques are known in the field. Either block-based motion estimation or optical flow-based motion estimation can be used to determine the overlapped area in each image pair. While motion estimation may involve a large amount of computations, a system according to the present invention may already use motion estimation in order to achieve high-efficiency image compression. Therefore, the use of motion estimation for determining overlapped area in image pair doesn't require any additional computations. The goal of motion estimation for image stitching is to determine the overlapped area. Therefore, a global motion vector will be sufficient for this purpose. Accordingly, the type of motion estimation required is global motion estimation. In case that local motion estimation is used, a global motion vector may be derived by processing the local motion vectors or motion fields. For example, a dominant motion vector may be chosen as the global motion vector. By identifying the overlapped area in image pair, feature-based or pixel-based image matching can be applied to the overlapped area to speed up the image matching process.

Figure 4B:
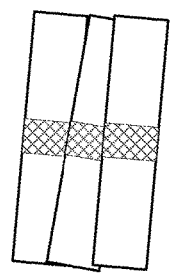
FIG. 4B illustrates the effect of camera tilt for a side-view capsule camera system.

The capsule may also tilt while travelling in the GI tract. Capsule tilt will cause the captured image to rotate with respect to the longitudinal direction. FIG. 4B illustrates an example of image rotation caused by camera tilt. Most motion estimation techniques assume a translational model and don't take into account of image rotation. In order to determine the capsule tilt, the motion estimation technique selected will be able to handle image rotation. Alternatively, image rotation can be intrinsically taken care of during image matching process since feature-based image matching often includes a rotation matrix in the image matching model. The capsule device may also be equipped with a gyroscope, accelerometer, or electronic compass to determine 3D capsule motion. In this case, capsule tilt and/or movement parameters can be read out and used to assist image stitching. In FIG. 4A and FIG. 4B, the images from two captures are fused to form a wide image. In an alternative configuration, two separate image sequences can be formed for two corresponding cameras. Image stitching can be performed on individual image sequence first. The two stitched composite images can then be fused to form a wide stitched composite image. An alternative solution is to stitch two images from two cameras at each time instance. This will be easier because of no changes occur in the scene while capturing the two intra images. Image stitching can then be performed on a wide stitched image sequence.

In the capsule camera system environment, the lighting source is provided and controlled by the capsule system. Therefore, the light condition is known. In one embodiment of the present invention, the light conditions for the images are stored. The lighting information can be retrieved and used to compensate the lighting variations during image stitching.

The images for stitching may be taken over a period of time. There may be object motion during this period. During image stitching, each area of the composite image may find its correspondence from multiple images. These corresponding areas are blended to obtain the final composite image in conventional image stitch for digital photography. Due to motion in the images, image blending based on average, median filter, or weighted sum will cause blurring (or double image). In order to create a non-blurred composite image for digital photography application, various advanced image blending techniques have been developed in the field. For example, image blending techniques named p-norm, Vornoi, weighted ROD vertex cover with feathering, graph cut seams with Poisson, Laplacian pyramid blending, gradient domain blending are presented in "Image Alignment and Stitching: A Tutorial", by Szeliski, Microsoft Research Technical Report MSR-TR-2004-92, Dec. 10, 2006. These advanced blending techniques usually select pixel or pixels for blending from one of the images based on a certain criterion. While such image blending techniques can generate non-blurred composite images, often some objects and local deformations in the composite image are not visible. Neither blurring nor missing objects is acceptable for the capsule image application. To overcome these issues, a system according to the present invention uses time-space representation for the composite image, which will be able to describe the time-varying nature of the stitched scene.

Considering the characteristics of the GI tract, in one embodiment of the present invention, captured images are preprocessed by applying color space transformation such as flexible spectral imaging color enhancement. This will improve the image feature visibility and stitching performance.

Given the nature of the bowel movement, capsule may stay in one place for a period of time and capture multiple images of the same scene. In one embodiment of the present invention, the difference of adjacent images can be used to remove redundant images. The lighting variance as well as gradient information can also be taken into consideration to evaluate difference of adjacent images. Accordingly, the size of the image sequence and reading time can be substantially reduced.

Time-Space Representation

In one embodiment of the present invention, the time-space representation displays a static composite image for each time instance which is selected by users. For example, at time index 1, all individual images will be warped onto the first image coordinates. By using the first image as a reference, the local deformation captured by the first image will show in the first composite image. A scrolling bar can be used to allow a user to browse time-space images at any time instance. By scrolling the bar to time index i, a new composite image with all individual images warped onto the ith image coordinates will show on the screen. Thus the local deformation captured by the ith image can be observed. No matter where the pointer of the scrolling bar is, the local deformation for the current time index will show on the screen and other images will be warped and adapted to current time as well.

For some sections of the GI tract which is not cleaned well, for example, food residues will appear in the images. They may not be useful from diagnostic point of view, but can provide significant image features. In one embodiment of present invention, color and pattern analysis will be applied to remove those areas from images before stitching. Same technique may also be applied to remove sessions with air or water bubbles. Machine learning algorithms can be applied to detect those unwanted image areas.

For some sections of the GI tract without significant image intensity and gradient features, shading information will be used to roughly estimate the surface depth. Pathological features such as subsurface tumors can be detected from the estimated depth map using this method. In one embodiment of the present invention, if such pathological features are detected, two images will be simply stacked together to avoid losing any information. Besides stacking two images, overlaying one image on top of the other one can be used to save both storage and reading time, if pathological features are not shown. A continuous time space representation can be generated according to the above method.

Figure 5:
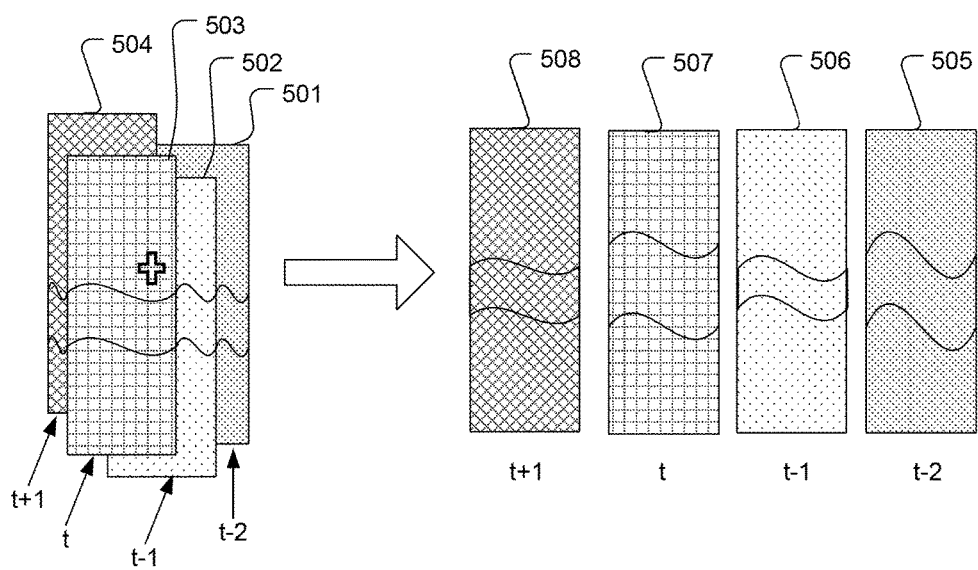
FIG. 5 illustrates an example of displaying multiple images captured from a capsule camera system according to an embodiment of the present invention, where the multiple images are warped to form a composite image.

In another embodiment of the present invention, images 501-504 correspond to warped images captured from t−2 to t+1, as shown in FIG. 5. The user has an option to review the original images 505-508 before warping. The original images can be originally captured image if the number of cameras is equal to one. Otherwise, the original image represents a composed image from intra images captured by multiple cameras. The user interface according to an embodiment of the present invention will display the composed image corresponding to images 501 to 504. The user can click any section of the composed image and all related original images 505-508 will be displayed then.

Figure 6:
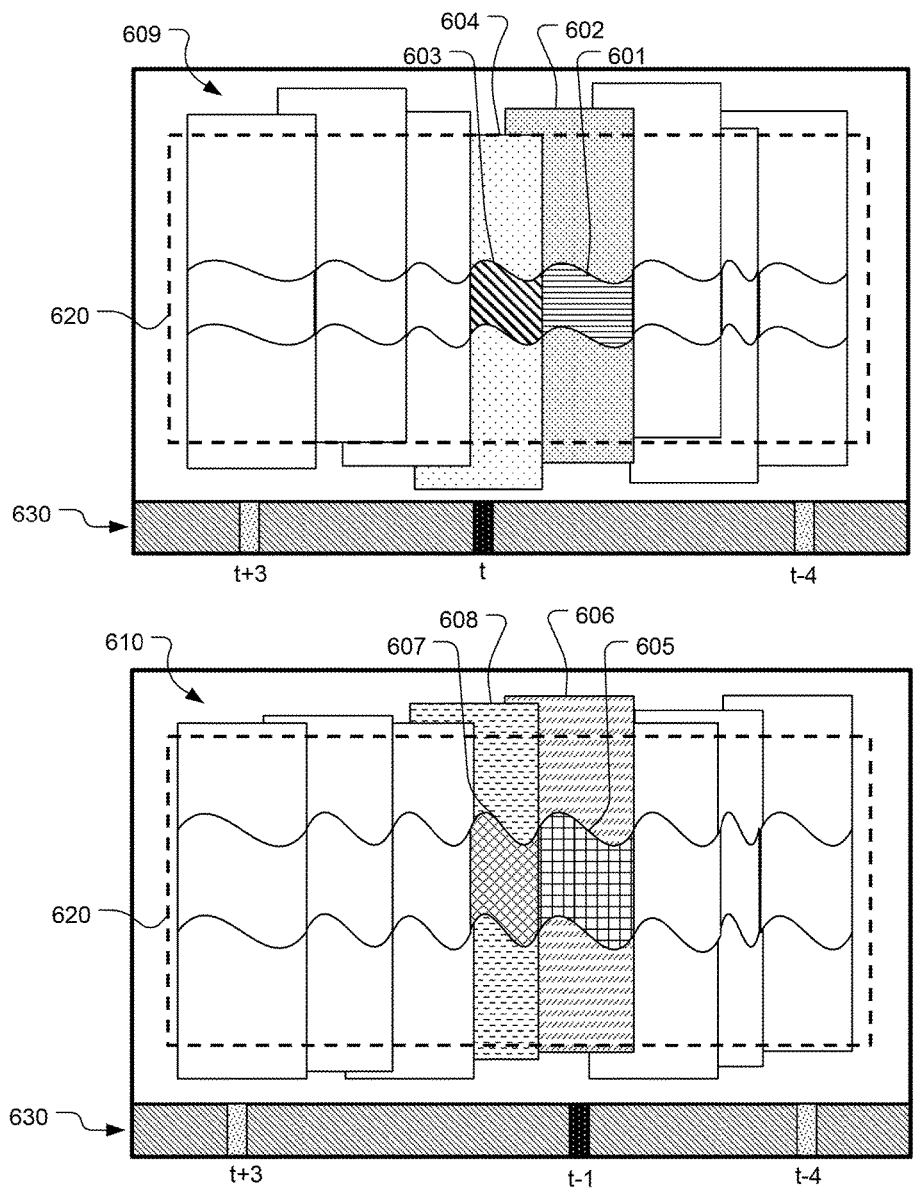
FIG. 6 illustrates an example of dynamic (time-space) representation of captured images with local deformation.

FIG. 6 shows an example of time-space representation according to an embodiment of the present invention for the composite image, when a user is browsing from time t to t−1 (backwards). While FIG. 6 illustrates an example of horizontal scrolling, vertical scrolling may also be implemented. Scroll bar 530 is provided to allow a user to scroll across the image sequence. Image 604 represents a single captured image or a composite image from multiple cameras captured at time t. Region 603 shows the local deformation at time t. Composite image 609 corresponds to all neighboring images captured from t−4 to t+3. The composite image is displayed in display window 620 as shown in FIG. 6. The number of neighboring images can be customized by the user. All neighboring images are warped by using image 604 at time t as a reference. Warped image 602 and warped local deformation region 601 corresponding to originally captured image at time t−1 (i.e., image 606 and region 605) are shown in FIG. 6 at the location where they should appear at time t. When users scroll the toolbar back to time index t−1, another composite image 610 will be displayed. In this image, all neighboring images are warped by using image 606 as a reference. Image region 605 shows the local deformation captured at time t−1. Warped image 608 and warped local deformation region 607 correspond to image originally captured at time t (i.e., image 604 and region 603) are shown in FIG. 6 at the location where they should appear at time t−1.

In the embodiment shown in FIG. 6, image stitching is performed in a dynamic fashion. For each section with local movement, the images are stitched for different time instances over a certain period. Since the capsule device travels relatively slow in the GI tract, each section may correspond to overlapped area among multiple consecutive images. Therefore, a time-space representation of a section with local movement can be presented.

In another embodiment of the present invention, the time-space representation display static composite images sequentially as a video. For example, instead of showing a static image at time t corresponding to composite image 609, an embodiment of the present invention may display a sequence of individual images from the composite image using each image captured from t−4 to t+3 as a reference. Accordingly, the user does not need to manually scroll back and forth. The time window of displaying the sequence of individual images, such as from t−4 to t+3, can be selected by users. A video including neighboring deformation will be displayed for better space-time visualization. The continuing, but smooth, motion of the stitched image resembles the natural bowel movement. The process for generating stitched images also reduces jerkiness associated with camera movement often noticed in conventional capsule video.

In one embodiment of the present invention, a user can specify the step while browsing the entire time-space display. For example, the current display window shows a composite image or a composite video for a series of neighboring images from time index t−4 to t+3 as shown in FIG. 6. When stepping forward, instead of stepping at a single frame starting from t−3 to t+4, the stepping may also advance to the next period of time which has overlap with the period from t−4 to t+3. For example, the stepping may go to a next period from t to t+8. This can reduce the reading time without losing information across the boundary of two display segments.

Figure 7:
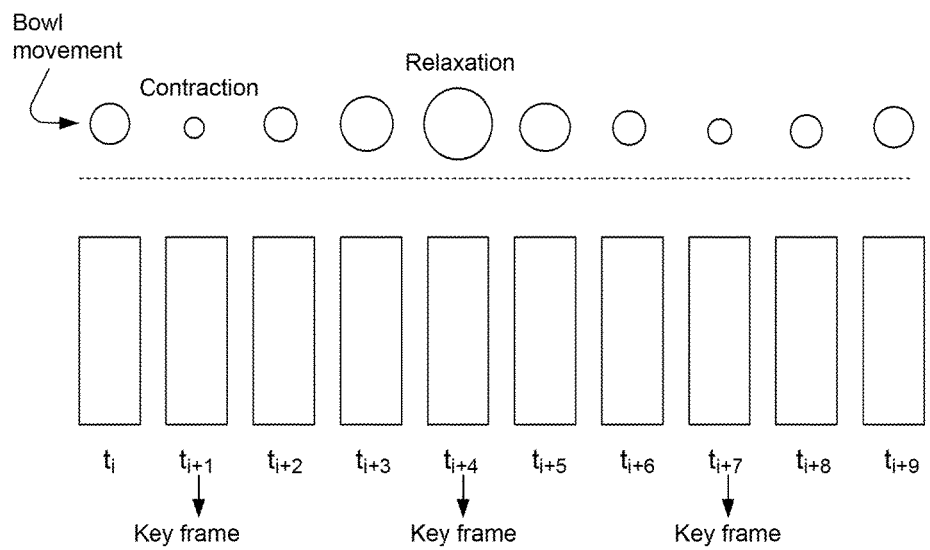
FIG. 7 illustrates an example of displaying multiple images captured from a capsule camera system according to an embodiment of the present invention, where key events are selected based on bowel movement.

In one embodiment of the present invention, instead of displaying composite images sequentially using each frame as a reference, a user can select key frames as references. One option to select key frames is based on the natural bowel movement. The largest contraction and relaxation of the GI tract can be considered as key events, such as frame ti+1, ti+4 and ti+7 in FIG. 7. Detecting such key events can be implemented by taking into account the variation of light sources. Accordingly, the variation of light source is tracked. To ensure constant lighting condition, the illumination from the capsule is automatically adjusted. When the GI tract contracts, the capsule is close to the wall and less illumination is needed. On the other hand, when the GI tract relaxes, the capsule is away from the wall and more illumination is required to provide good image quality. By selecting a reflectance model for the environmental tissues (e.g., a Lambertian surface), a relationship between image intensity, incoming near-field lighting intensity and the distance between the light source and the wall surface can be described according to the following equation:

$$I = \varphi\left(\sum_{i=1}^{V} \rho \cdot \frac{\vec{L_i} \cdot \vec{n}}{\gamma_i^2}\right) \quad (4)$$

where I represents the image intensity, $\varphi$ is a camera response function mapping the surface radiance to the image intensity, $\rho$ is the surface albedo representing the reflectance property of the surface. Assume there are V light sources, the total surface radiance is a sum of contribution from all light sources. $\vec{L_i}$ is the intensity/strength of ith light source, $\vec{n}$ is the surface normal, $\gamma_i$ is the distance between the light source and the surface scene point. If the orientation of the light source does not change when the light source is adjusted, the angle between the incoming lighting and surface normal will remain the same. The farther the distance is, the darker the surface radiance is and the more illumination is needed. By tracking the change of illumination, contraction and relaxation of the GI tract can be detected. Therefore the frames corresponding to the largest and smallest illumination observed can be used as key frames. The effect of exogenous content, especially fecal content are removed in advance to avoid the effect to computing light intensity/image intensity. The fecal content can be identified by ratio of different color and/or other means. Detecting such key frames is not limited to the method mentioned above. For example, machine learning method can also be used to detect different bowel movement patterns. The time-space representation described above reduces the reading time and provides a more concise display of the GI tract.

Figure 8:
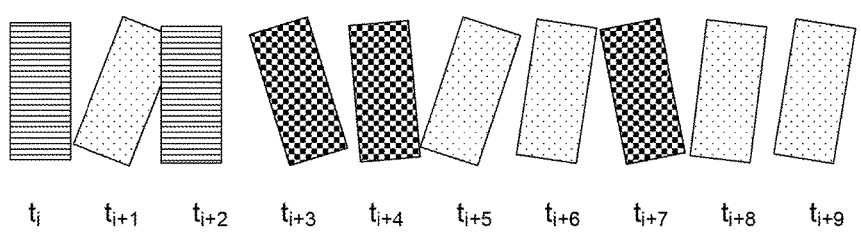
FIG. 8 illustrates an example of displaying multiple images captured from a capsule camera system according to an embodiment of the present invention, where key events are selected based on rotation angle.

In another embodiment of the present invention, instead of using bowel movement to select key frames, the angle of capsule's rotation can be used to represent key events since viewing from different angles can provide different information to a user. Given the computed transformation H between adjacent images and calibrated camera intrinsic matrix K, rotation angle between adjacent images can be estimated based on Eq. (3). By selecting an image automatically or manually by a user as a reference, these rotation angles can be categorized into several classes as showed in FIG. 8. Images ti and ti+2 belong to group 1, images ti+1, ti+5, ti+6, ti+8, and ti+9 belong to group 2, and images ti+3, ti+4, and ti+7 belong to group 3. One frame from each group can be selected as a key frame. In addition, all these frames can be selected from a time window, where the size is pre-defined or selected by the user.

Figure 9:
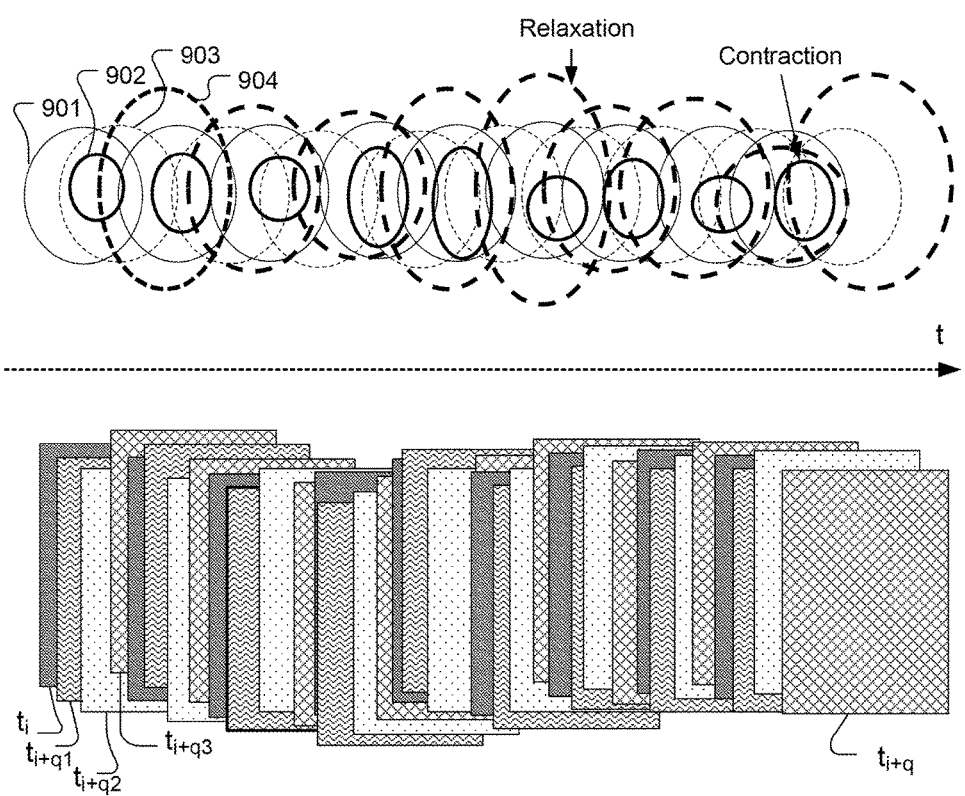
FIG. 9 illustrates an example of displaying multiple images captured from a capsule camera system according to an embodiment of the present invention, where bowel movement status is categorized into multiple phases and images associated with each phase are grouped.

In one embodiment of the present invention as shown in FIG. 9, bowel status 901 illustrates the intermediate status of bowel movement from relaxation to contraction. Bowel status 902 (bold circle) illustrates contraction of the GI tract. Bowel status 903 (dashed circle) illustrates the intermediate status of bowel movement from contraction to relaxation. Bowel status 904 (bold dashed circle) illustrates relaxation of the GI tract. The bowel movement can be categorized into several phases. For example, phase I represents contraction (902), phase II represents relaxation (904), and phase III represents neutral status (901 and 903). Image ti corresponding to bowel status 901 is captured at time ti. Image ti+q1 corresponding to bowel status 902 is captured at time ti+q1. Image ti+q2 corresponding to bowel status 903 is captured at time ti+q2. Image ti+q3 corresponding to bowel status 904 is captured at time ti+q3. Capsule image capturing usually takes place several times each second. Therefore, the capsule does not travel much during this time window from ti to ti+q. If the images are grouped according to the phase of peristalsis (i.e., status of bowel contraction/relaxation), images in each group may still have enough overlap even if they are not continuous in the temporal direction. Instead of using all the images in this time window from ti to ti+q for stitching as mentioned above, image stitch can be performed for each group/phase. For the entire time window, only a few stitched images for a few different phases need to be shown. Number of phases reflects how much detailed phase change will be displayed, which can be determined by the user. Accordingly, stitched images with ghost effects due to large deformation between different phases can be avoided.

Figure 10:
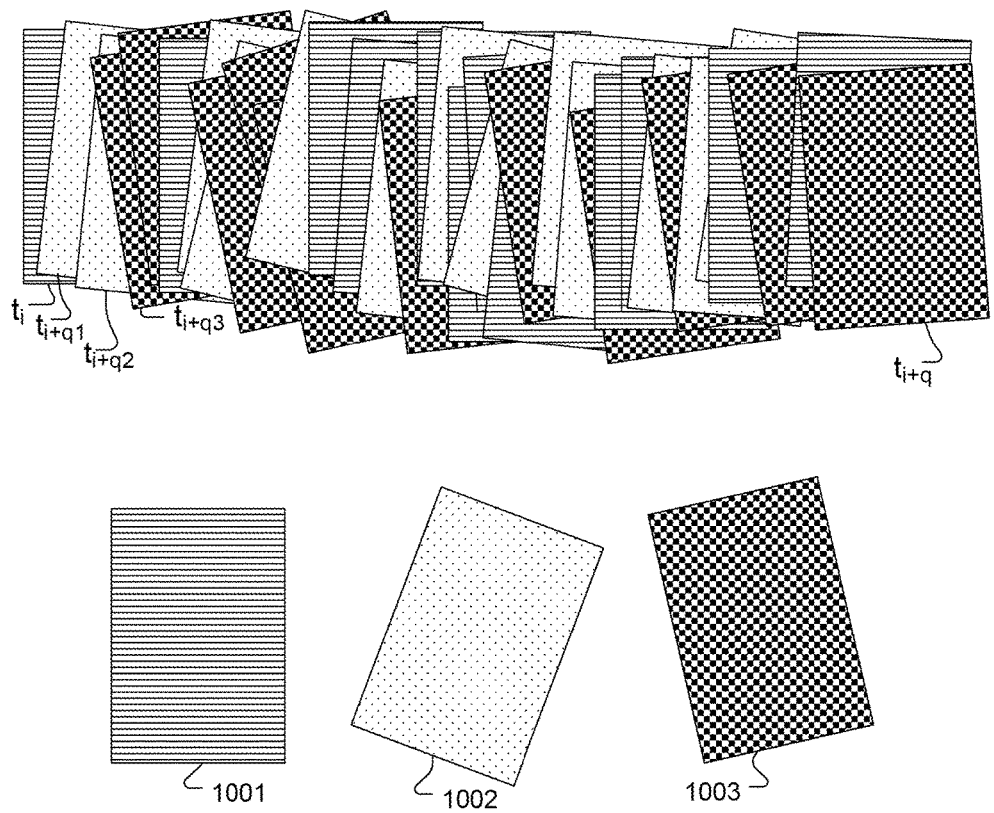
FIG. 10 illustrates an example of displaying multiple images captured from a capsule camera system according to an embodiment of the present invention, where images having similar rotation angle are grouped to form a composite image.

In another embodiment of the present invention as shown in FIG. 10, key images 1001-1003 correspond to three images captured from different angles due to the rotation of the capsule. At a normal capture frequency, the capsule does not travel much during this time window from ti to ti+q. If images are grouped according to different angles, images in each group still have enough overlap even though they are not continuous in the temporal direction. Instead of using all the images in this time window from ti to ti+q for stitching as mentioned earlier, only images for each group/angle are stitched. For the entire time window, only three stitched images are needed for three different angles. The number of angles reflects how much detailed angle change will be displayed, which can be determined by the user. The reference image used to compute the angles between adjacent images can be determined by the user. Accordingly, stitched images with ghost effects due to large ambiguity between different view directions can be avoided.

Figure 11:
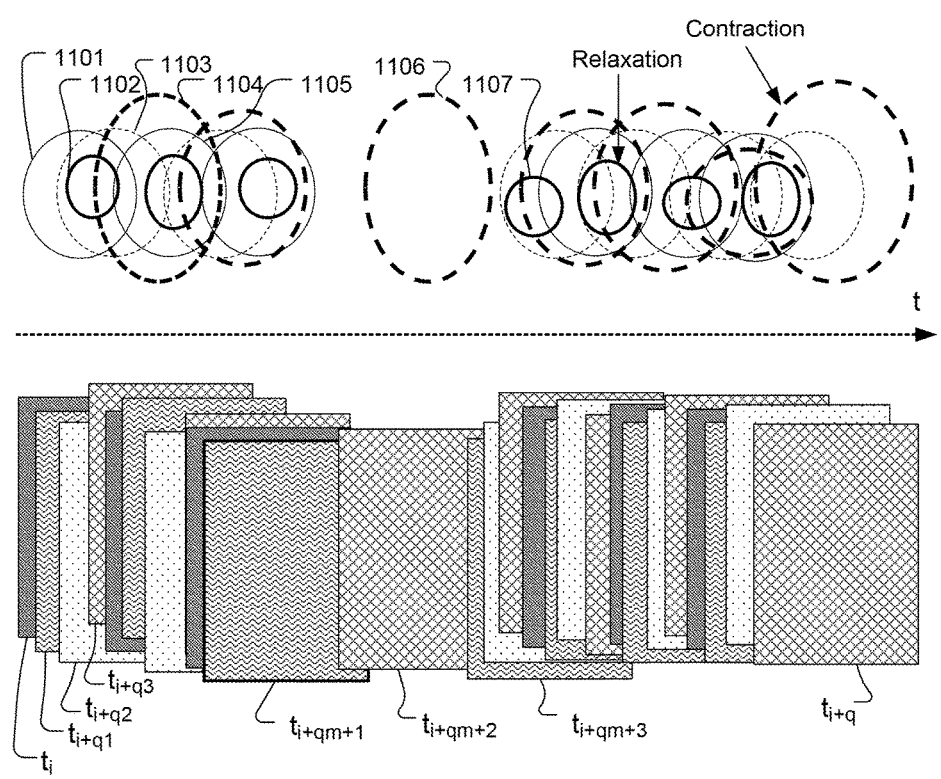
FIG. 11 illustrates an example of displaying multiple images captured from a capsule camera system according to an embodiment of the present invention, where bowel movement status is categorized into multiple phases and images associated with one phase may have gaps with adjacent images in the group.

Another embodiment of the present invention is shown in FIG. 11. Bowel status 1101 illustrates the intermediate status of bowel movement from relaxation to contraction. Bowel status 1102 (bold circle) illustrates contraction of the GI tract. Bowel status 1103 (dashed circle) illustrates the intermediate status of bowel movement from contraction to relaxation. Bowel status 1104 (bold dashed circle) illustrates relaxation of the GI tract. The bowel movement can be categorized into multiple phases. For example, phase I represents contraction 1102, phase II represents relaxation 1304, and phase III represents neutral status (1101 and 1103). Image ti corresponding to bowel status 1101 is captured at time ti. Image ti+q1 corresponding to bowel status 1102 is captured at time ti+q1. Similarly, images ti+q2 and ti+q3 corresponding to bowel status 1103 and 1104 are captured at time ti+q2 and ti+q3 respectively. Image ti+qm+1 corresponding to bowel status 1105 is captured at time ti+qm+1. Image ti+qm+2 corresponding to bowel status 1106 is captured at time ti+qm+2. Image ti+qm+3 corresponding to bowel status 1107 is captured at time ti+qm+3. From ti+qm+1 to ti+qm+3, the capsule only captures images associated with phase I and III due to several reasons such as bad images, occlusions, etc. Therefore, when stitching is performed for images associated with the phase II, there will be a gap from ti+qm+1 to ti+qm+3. When the gap is too big to generate any overlap between two adjacent phase-II images, the stitched images will be separated into two parts for display.

Figure 12:
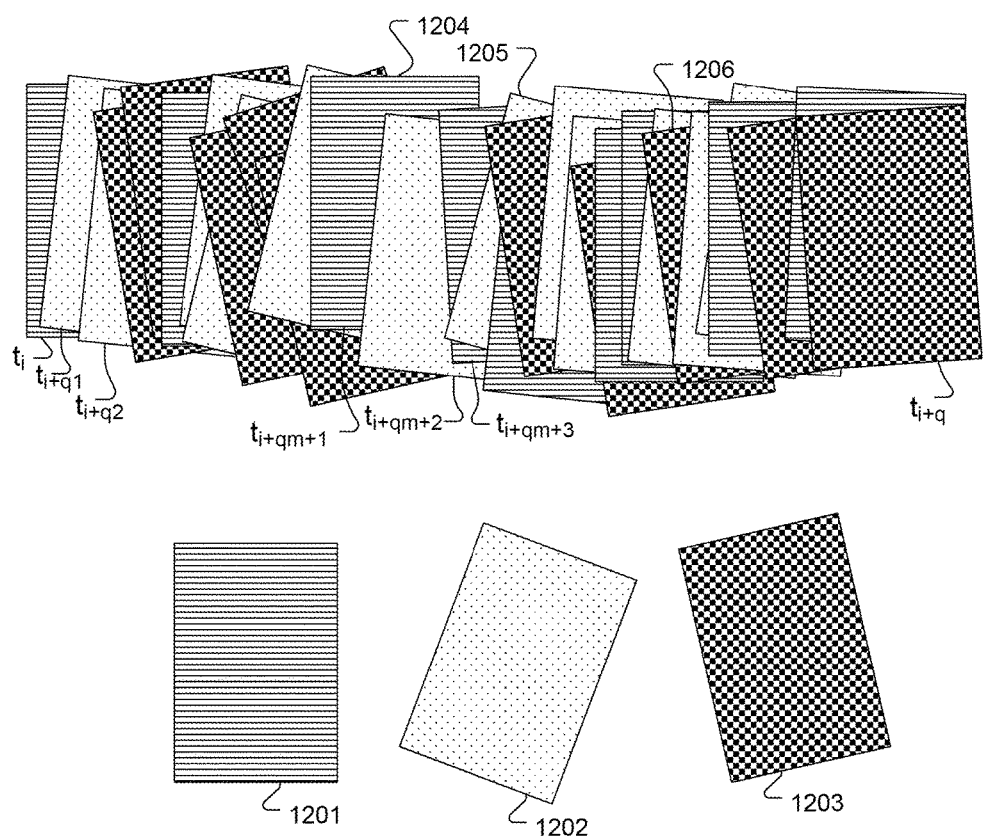
FIG. 12 illustrates an example of displaying multiple images captured from a capsule camera system according to an embodiment of the present invention, where rotation angle is categorized into multiple phases and images associated with one phase may have gaps with adjacent images in the group.

In another embodiment of the present invention as shown in FIG. 12, key images 1201 to 1203 represent three images captured from different angle due to the rotation of the capsule. In a normal capture frequency, the capsule does not travel much during the time window from ti to ti+q. If the images are grouped according to the rotation angle, images in each group still have enough overlap even though they are not continuous in the temporal direction. In this case, for a time window from ti+qm+1 to ti+qm+3, only images corresponding to two angle groups are captured because the capsule does not rotate 180° very often while traveling forwards. Images 1204 and 1206 belong to the same group as image 1203. Image 1205 belongs to the same group as image 1202. Therefore when the images are stitched for the group that image 1201 belongs; there will be a gap from ti+qm+1 to ti+qm+3. When the gap is too big to generate any overlap between two adjacent images in this group, the stitched images are separated into two parts for display according to an embodiment of the present invention.

In one embodiment of the present invention, image matching is applied prior to grouping images according to angle or phase. The image at the group boundary will be matched with adjacent images in respective groups. The image will be assigned to the group with the best match.

In another embodiment of the present invention, statistical information can be used for image grouping. A statistic distribution of image phases or angles is computed within a time window, such as ti to ti+q in FIGS. 9 to 12. The number of local maximum can be used to group images according to the statistics. The stitched images provides a best representation corresponding to the originally captured angles or phases.

Figure 13A:
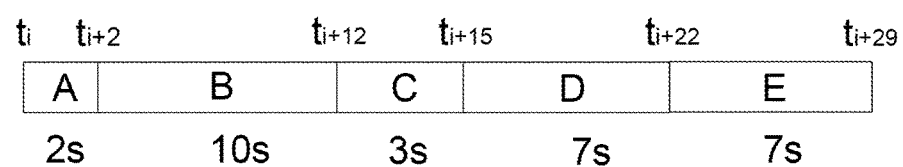
FIG. 13A illustrates an exemplary image sequence having multiple local deformations.
Figure 13B:
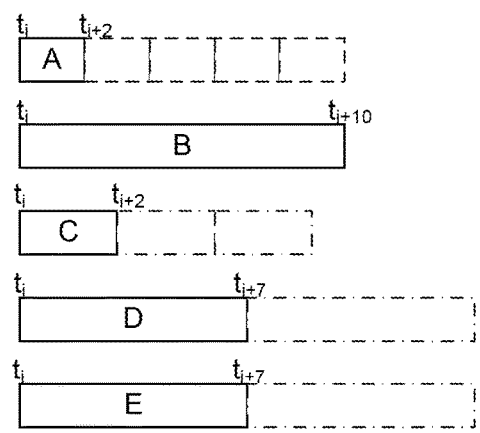
FIG. 13B illustrates an example of displaying multiple images captured from a capsule camera system according to an embodiment of the present invention, where segments of images corresponding to local deformations are displayed concurrently.

In one embodiment of the present invention, the sections with local deformation are displayed one at a time. For example, blocks A, B, C, D and E represent different local deformations in different time segments of an image sequence as shown in FIG. 13A. Segment A corresponds to deformation occurring from $t_i$ to $t_{i+2}$, segment B corresponds to deformation occurring from $t_{i+2}$ to $t_{i+12}$, segment C corresponds to deformation occurring from $t_{i+12}$ to $t_{i+15}$, segment D corresponds to deformation occurring from $t_{i+15}$ to $t_{i+22}$, and segment E corresponds to deformation occurring from $t_{i+22}$ to $t_{i+29}$. The longest deformation is B which lasts for 10 seconds. However, the user may need to spend 29 seconds to observe all local deformations. If the total number of images in these segments is very large, it may take a long time to animate all the local deformations associated with these segments. To speed up the dynamic display, the segments with local deformation can be divided into multiple groups, where each group consists of same deformation as illustrated in FIG. 13A. For example, segment A represents the contraction of the GI tract and segment B represents the relaxation of the GI tract. This can be achieved by applying local deformation detection and segmentation on the composite images within these segments. The groups can be displayed in motion concurrently and the segment associated with each group can be played back one at a time, as illustrated in FIG. 13B. After segmentation, segments A, B, C, D and E can be displayed starting at the same time. The display of shorter sections such as segment A can be repeated for several times as shown in FIG. 13B. Accordingly, the display time required can be substantially reduced. The example in FIG. 13B illustrates the case that the display time can be reduced from 29 seconds to 10 seconds. Blending across the boundary of adjacent groups can be applied to ensure a smooth display.

Figure 14A:
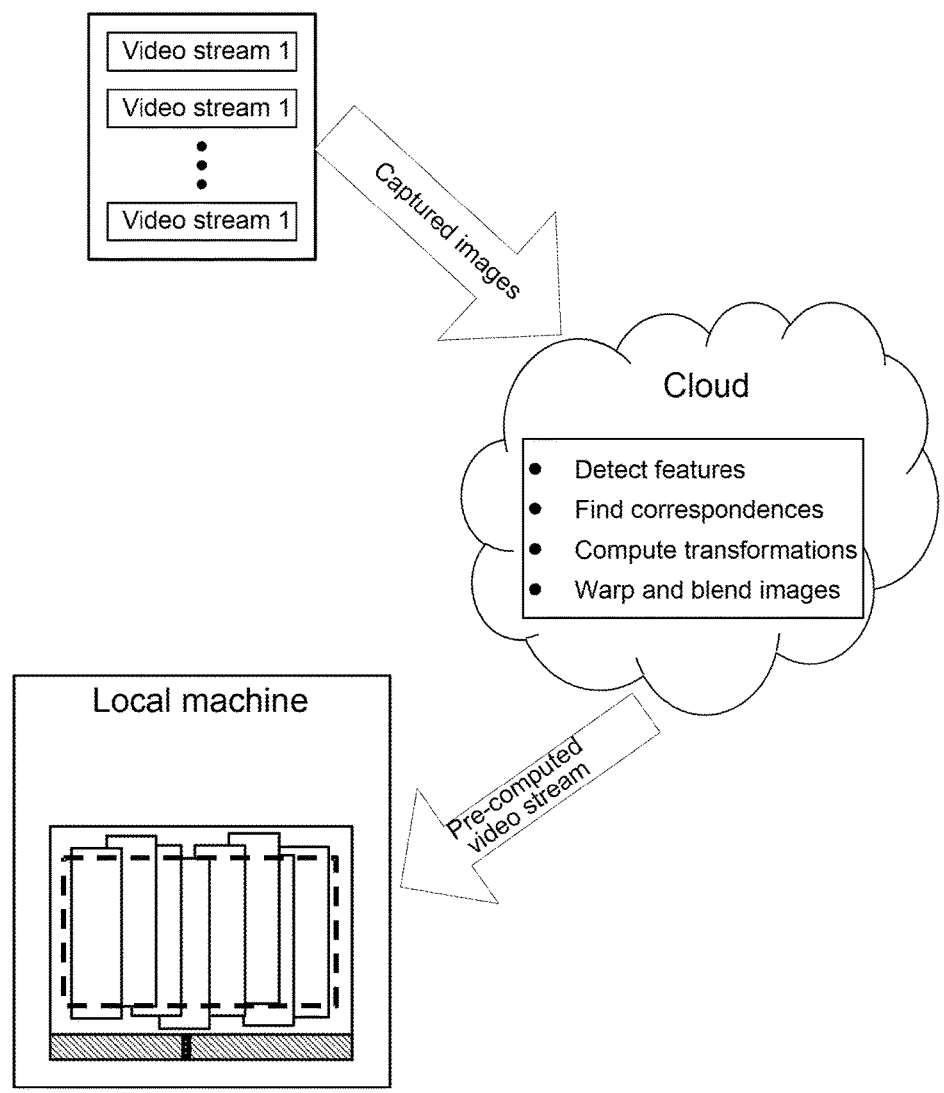
FIG. 14A illustrates an example of computing stitched images in cloud and sending the final video to the client.
Figure 14B:
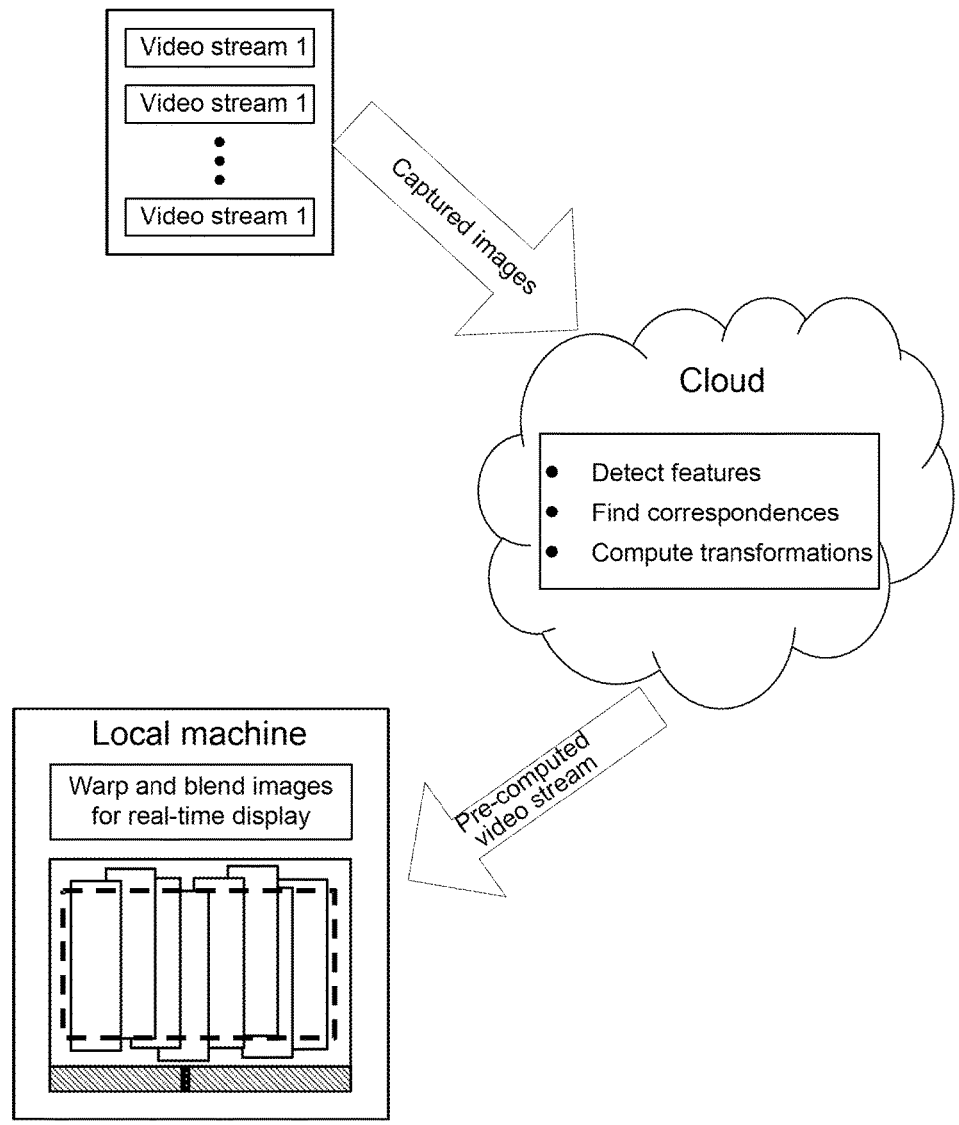
FIG. 14B illustrates an example of computing all transformation between image pairs in cloud and apply real time image warping and blending on the client machine.

In one embodiment of the present invention, cloud based computing can be used to reduce the computational load on local machines, as illustrated in FIG. 14A. Once the capsule is retrieved, all the captured images can be uploaded to cloud. All computations such as detecting features, computing image correspondence and transformations, and warping and blending images, can be implemented in cloud. The pre-computed multiple video streams consisting of stitched big images can then be downloaded to a local machine for display. Compared to the original video size, each frame of the new video corresponds to a composite image consisting of u×v original images, where u is the number of frames captured by each camera and v is the number of cameras. Thus the new video requires a tremendous storage space and/or takes a long time to download. To solve this problem, only transformations between all image pairs are computed in cloud. Blending and final rendering of each composite image are performed on local machines as shown FIG. 14B.

Extension to 360° Full View Panoramic Capsule Using Four Cameras

Figure 15:
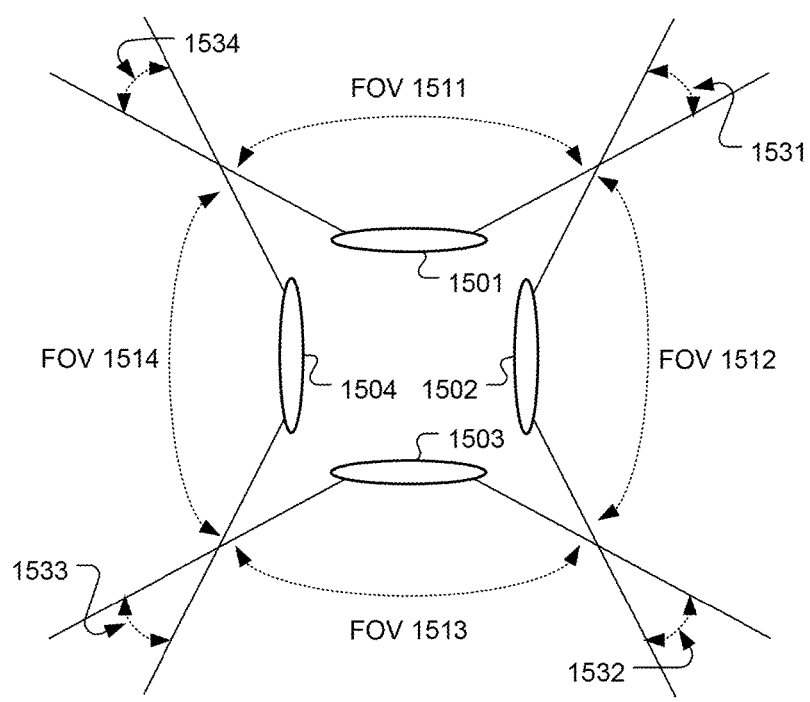
FIG. 15 illustrates an example of four-camera configuration with overlapped FOVs between two neighboring cameras to form a 360° full-view panoramic image.

FIG. 1A illustrates an example of two cameras with overlapped FOVs. In one embodiment of the present invention, four cameras are used as shown in FIG. 15. The four cameras are configured so that the FOV centers of two neighboring cameras are separated by 90° substantially. The four lenses (1501-1504) for the four cameras have respective FOVs 1511-1514. Two neighboring FOVs have overlapped areas 1531-1534. The four cameras are configured to cover an aggregated 360° FOV.

The system is configured to capture images from the four cameras substantially at the same time. A scene in the overlapped area is simultaneously captured by two neighboring cameras. As mention previously, the intra-image based pose estimation can be used to improve the accuracy of pose estimation for the two neighboring cameras. The four FOVs are wrapped around and there are four overlapped areas among the four lenses. The intra-image based pose estimation can be extended to include the fact that the four FOVs cover 360°. For example, the images associated with the overlapped region in 1531 can be used to help pose estimated for cameras associated with lenses 1501 and 1502. The images associated with the overlapped region in 1532 can be used to help pose estimated for cameras associated with lenses 1502 and 1503. The images associated with the overlapped region in 1533 can be used to help pose estimated for cameras associated with lenses 1503 and 1504. Furthermore, the images associated with the overlapped region in 1534 can be used to help pose estimated for cameras associated with lenses 1504 and 1501. The round of intra-image based pose estimation makes a circle. If there is any discrepancy between pose estimation based on images associated with lens 1501 and pose estimation based on the circular chain, the error can be adjusted by iterating pose estimation through another circular chain.

Figure 16A:
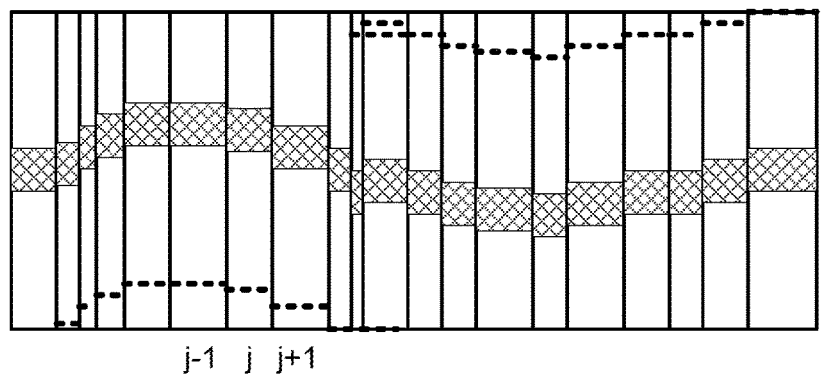
FIG. 16A illustrates the effect of capsule spin and translation for 360° full-view panoramic images.
Figure 16B:
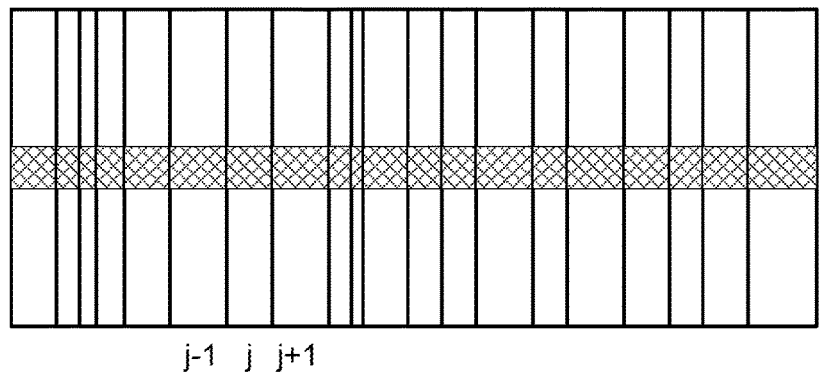
FIG. 16B illustrates an example of rotation compensation for 360° full-view panoramic images.

When the capsule travels through the GI tract, the capsule may spin. The effect of capsule spin will cause the captured images shifted up and down as shown in FIG. 4A. For the 360° full-view panoramic capsule, the composed wide image from four cameras corresponds to a full-view panoramic image. When the capsule spins, the captured images will be shifted cyclically in the vertical direction as shown in FIG. 16A. The shaded areas correspond to the fused areas between two cameras. For the full-view panoramic images, there are four fused areas. Nevertheless, for simplicity, only one fuse area in each image is shown. The capsule spin can be detected by motion estimation. The dashed lines indicate the relative image edge with respective to the first image. An embodiment of the present invention uses global motion estimation to determine the amount of camera spin and the spin can be compensated. FIG. 16B illustrates an example of rotation compensated images. The capsule device may also be equipped with a gyroscope, accelerometer, or electronic compass to determine camera rotation. The capsule rotation information can be read out from the device and used for rotation compensation.

The invention may be embodied in other specific forms without departing from its spirit or essential characteristics. The described examples are to be considered in all respects only as illustrative and not restrictive. Therefore, the scope of the invention is indicated by the appended claims rather than by the foregoing description. All changes which come within the meaning and range of equivalency of the claims are to be embraced within their scope.

The invention claimed is:

1. A method of displaying images of human gastrointestinal (GI) tract captured using a capsule device including a plurality of cameras, wherein the plurality of cameras are configured fixedly within a capsule housing and any two neighboring cameras of the plurality of cameras have an overlapped field of view (FOV), the method comprising:
receiving a plurality of image sequences captured by the plurality of cameras respectively, wherein the plurality of image sequences comprise multiple sets of Intra images and an i-th set of Intra images corresponds to concurrent images captured by the plurality of camera at time index i, and where two different sets of intra images correspond to two difference time instances;
generating wide images based on the multiple sets of Intra images by stitching image members in each set of Intra images to form one wide image;
generating a composite image by stitching wide images corresponding to the multiple sets of Intra images; and
displaying the composite image on a display device.

2. The method of claim 1, wherein differences between adjacent wide images in the plurality of image sequences are used to determine a redundant wide image and the redundant wide image is excluded from said stitching the wide images.

3. The method of claim 2, wherein light variation or gradient information of the adjacent wide images is taken into account for determining the differences between the adjacent wide images.

4. The method of claim 1, wherein features are detected for two neighboring wide images in the plurality of image sequences and said stitching the multiple sets of Intra wide images excludes at least one of the two neighboring wide images if the features for the two neighboring wide images are distinct.

5. The method of claim 4, wherein the two neighboring wide images are displayed in separate display areas on the display device if the features for the two neighboring wide images are distinct.

6. The method of claim 1, wherein camera tilt parameter, camera rotation parameter, or camera motion parameter is used to assist said stitching the wide images.

7. The method of claim 6, wherein the camera tilt parameter, camera rotation parameter, or camera motion parameter is determined based on motion estimation.

8. The method of claim 6, wherein the camera tilt parameter, camera rotation parameter, or camera motion parameter is determined by a gyroscope, accelerometer, or electronic compass equipped with the capsule device.

9. The method of claim 1, wherein said stitching the wide images comprises compensating lighting variation within the plurality of image sequences based on light condition, wherein the light condition associated with the light condition is retrieved from the capsule device.

10. The method of claim 1, wherein an image area containing air or water bubbles is excluded from said stitching the wide images.

11. The method of claim 1 further comprising warping the multiple sets of Intra images of the plurality of image sequences based on the set of Intra images with a selected time index to generate a multiple sets of warped Intra images with respect to the set of Intra images with the selected time index, wherein said generating the composite image is performed for the selected time index, said stitching the wide images corresponding to the multiple sets of Intra images is based on the multiple sets of warped Intra images with respect to the set of Intra images corresponding to the selected time index, and said displaying the composite image corresponds to displaying the composite image for the selected time index.

12. The method of claim 11, whether the selected time index is selected by a user through a user interface.

13. The method of claim 11, wherein said warping the multiple sets of Intra images of the plurality of image sequences based on the set of Intra images with the selected time index and said displaying the composite image for the selected time index are performed for each selected time index within a range of time indexes.

14. The method of claim 13, wherein the range of time indexes is selected by a user through a user interface.

15. The method of claim 11, wherein image features associated with the plurality of image sequences are extracted for said warping the multiple sets of Intra images of the plurality of image sequences or said stitching the multiple sets of warped Intra images.

16. The method of claim 15, wherein the image features associated with the plurality of image sequences are extracted based on intensity, gradient or shading information of the multiple sets of Intra images.

17. The method of claim 15, wherein a color transformation is applied to the plurality of image sequences to enhance visibility of the image features.

18. The method of claim 15, wherein feature matching between the image features associated with two adjacent images of one set of Intra images are based on a transformation model and camera pose parameters associated with the plurality of cameras are used to initialize the transformation model.

19. The method of claim 18, wherein the camera pose parameters associated with the plurality of cameras are derived using calibration images stored in the capsule device and the camera pose parameters derived are stored in the capsule device.

20. The method of claim 15, wherein an overlapped area between two neighboring images in one image sequence is identified in order to speed up image matching based on the image features, wherein motion estimation is used to determine the overlapped area.

21. The method of claim 20, wherein global motion estimation is used to determine the overlapped area.

22. A method of displaying images of human gastrointestinal (GI) tract captured using a capsule camera, the method comprising:

receiving an image sequence comprising images captured by the capsule camera at different time instances;

selecting a set of key images from the image sequence according to an image characteristic associated with each image in the image sequence;

warping images in the image sequence based on one key image to generate warped images with respect to said one key image;

stitching the warped images corresponding to the different time instances to generate a composite image; and displaying the composite image for said one key image.

23. The method of claim 22, wherein the images in the image sequence are divided into multiple groups according to the image characteristic.

24. The method of claim 23, wherein one key image is selected from each of the multiple groups.

25. The method of claim 24, wherein said stitching the warped images is based on the warped images belonging to a same group as said one key image.

26. The method of claim 25, wherein if a gap exists in the images of the same group, the composite image associated with said one key image is separated into two parts to display, where the two parts correspond to images of the same group on two sides of the gap.

27. The method of claim 22, wherein the image characteristic corresponds to phase of peristalsis associated with each image in the image sequence.

28. The method of claim 27, wherein the phase of peristalsis associated with each image is determined from light intensity emitted by the capsule camera and image intensity of each image.

29. The method of claim 27, wherein the phase of peristalsis associated with each image is determined using machine learning.

30. The method of claim 22, wherein the image characteristic corresponds to an angle of capsule rotation associated with each image in the image sequence.

31. The method of claim 30, wherein the angle of capsule rotation is determined using motion estimation based on neighboring images.

32. The method of claim 30, wherein the angle of capsule rotation is determined by a gyroscope, accelerometer, or electronic compass equipped with the capsule camera.

33. The method of claim 22, wherein said one key image is determined based on natural bowel movement, largest illumination observed or smallest illumination observed.

* * * * *